(12) United States Patent
Rosentreter et al.

(10) Patent No.: US 7,129,255 B2
(45) Date of Patent: Oct. 31, 2006

(54) SUBSTITUTED 2-CARBA-3,5-DICYANO-4-ARYL-6-AMINOPYRIDINES AND THE USE OF THE SAME AS SELECTIVE LIGANDS OF THE ADENOSINE RECEPTOR

(75) Inventors: Ulrich Rosentreter, Wuppertal (DE); Thomas Krämer, Wuppertal (DE); Andrea Vaupel, Riehen (CH); Walter Hübsch, Wuppertal (DE); Nicole Diedrichs, Wuppertal (DE); Thomas Krahn, Hagen (DE); Klaus Dembowsky, Boston, MA (US); Johannes-Peter Stasch, Solingen (DE); Mitsuyuki Shimada, Nara (JP)

(73) Assignee: Bayer Aktiengesellschaft, Leverkusen (DE)

( * ) Notice: Subject to any disclaimer, the term of this patent is extended or adjusted under 35 U.S.C. 154(b) by 261 days.

(21) Appl. No.: 10/473,371

(22) PCT Filed: Mar. 25, 2002

(86) PCT No.: PCT/EP02/03303

§ 371 (c)(1),
(2), (4) Date: Jan. 7, 2004

(87) PCT Pub. No.: WO02/079196

PCT Pub. Date: Oct. 10, 2002

(65) Prior Publication Data

US 2004/0110946 A1    Jun. 10, 2004

(30) Foreign Application Priority Data

Mar. 30, 2001  (DE) ................. 101 15 945

(51) Int. Cl.
*A61K 31/44*  (2006.01)
*C07D 213/85*  (2006.01)
(52) U.S. Cl. ...................... 514/344; 546/287
(58) Field of Classification Search ............... 546/267; 514/344
See application file for complete search history.

(56) References Cited

U.S. PATENT DOCUMENTS 2,914,534 A  *  11/1959  Middleton ............... 546/287

FOREIGN PATENT DOCUMENTS

| EP | 0282904 | 9/1988 |
|---|---|---|
| EP | 0705820 | 4/1996 |
| WO | 9727177 | 7/1997 |
| WO | 9919302 | 4/1999 |
| WO | 0125210 | 4/2001 |
| WO | 0162233 | 8/2001 |

OTHER PUBLICATIONS

Olah, M.E. et al., "Cloning expression, and characterization of the unique bovine A1 adenosine receptor. Studies on the ligand binding site by site-directed mutagenesis." J. Biol. Chem. 267 pp. 10764-10770 (1992).

Klotz, K.N. et al., "Comparative pharmacalogy of human adenosine receptor subtypes—characterization of stably transfected receptors in CHO Cells," Naunyn Schmiedebergs Arch. Pharmacol. 357 1-9 (1998).

Poulsen, S.A. et al., "Adeonosine Receptors: New Opportunities for Future D rugs", Bioorganic and Medicinal Chemistry, 6 619-641 (1998).

Broadley, K.J., "Drugs modulating adenosine receptors as potential therapeutic agents for cardiovascular diseases." Exp. Opin. Ther. Patents, 10 1669-1692 (2000).

* cited by examiner

Primary Examiner—Zinna N. Davis

(57) ABSTRACT

This application relates to compounds of the formula

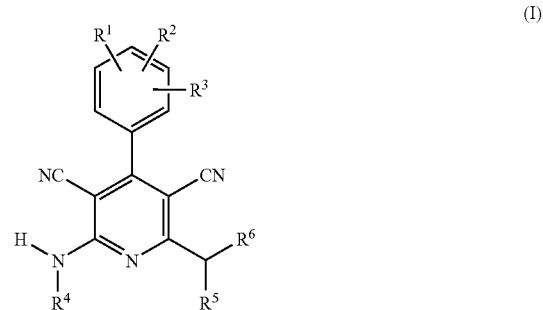

(I)

wherein the groups $R^1$–$R^6$ are as defined in the specification and claims, and to a pharmaceutical composition containing the same, and to a method of using the same in treatment of cardiovascular disorders.

6 Claims, No Drawings

SUBSTITUTED 2-CARBA-3,5-DICYANO-4-ARYL-6-AMINOPYRIDINES AND THE USE OF THE SAME AS SELECTIVE LIGANDS OF THE ADENOSINE RECEPTOR

The present invention relates to substituted 2-carba-3,5-dicyano-4-aryl-6-aminopyridines, to a process for their preparation and to their use as medicaments.

Adenosine, a nucleoside consisting of adenine and D-ribose, is an endogenous factor having cell-protective activity, in particular under cell-damaging conditions with limited oxygen and substrate supply, such as, for example, in the case of ischemia in various organs (for example heart and brain).

Adenosine is formed intracellularly as an intermediate during the degradation of adenosine-5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the heart rate, on the release of neurotransmitters and on lymphocyte differentiation.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to A1 or A3 receptors results in a decrease of the intracellular cAMP concentration via inhibition of adenylate cyclase.

According to the invention, "adenosine-receptor-selective ligands" are substances which bind selectively to one or more subtypes of the adenosine receptors, thus either mimicking the action of adenosine (adenosine agonists) or blocking its action (adenosine antagonists).

According to their receptor selectivity, adenosine-receptor-selective ligands can be divided into different categories, for example ligands which bind selectively to the A1 or A2 receptors of adenosine and in the case of the latter also, for example, those which bind selectively to the A2a or the A2b receptors of adenosine. Also possible are adenosine receptor ligands which bind selectively to a plurality of subtypes of the adenosine receptors, for example ligands which bind selectively to the A1 and the A2, but not to the A3 receptors of adenosine.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis." in J. Biol. Chem. 267 (1992) pages 10764–10770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells" in Naunyn Schmiedebergs Arch. Pharmacol. 357 (1998) pages 1–9, the disclosure of which is hereby fully incorporated by way of reference).

The "adenosine-receptor-specific" ligands known from the prior art are mainly derivatives based on natural adenosine (S.-A. Poulsen and R. J. Quinn, "Adenosine receptors: new opportunities for future drugs" in Bioorganic and Medicinal Chemistry 6 (1998) pages 619 to 641; K. J. Broadley, "Drugs modulating adenosine receptors as potential therapeutic agents for cardiovascular diseases" in Exp. Opin. Ther. Patents 10 (2000) pages 1669–1692). However, most of the adenosine ligands known from the prior art have the disadvantage that their action is not really receptor-specific, that their activity is less than that of natural adenosine or that they have only very weak activity after oral administration. Thus they are mainly used only for experimental purposes.

It is an object of the present invention to find or provide pharmacologically active substances suitable for the prophylaxis and/or treatment of various disorders, in particular disorders of the cardiovascular system (cardiovascular disorders), the substances preferably acting as adenosine-receptor-selective ligands.

The present invention relates to compounds of the formula (I)

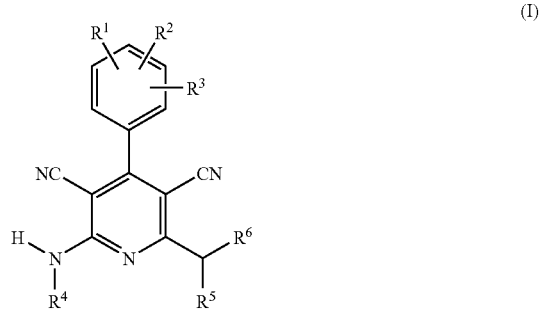

in which $R^1$, $R^2$ and $R^3$ independently of one another represent $(C_1-C_8)$-alkyl which may be substituted up to three times by hydroxyl, $(C_1-C_4)$-alkoxy, $(C_3-C_7)$-cycloalkyl, $(C_2-C_4)$-alkenyl, $(C_2-C_4)$-alkynyl, halogen or $(C_6-C_{10})$-aryloxy, $(C_6-C_{10})$-aryl which may be substituted up to three times by halogen, nitro, $(C_1-C_4)$-alkoxy, carboxyl, $(C_1-C_4)$-alkoxycarbonyl or mono- or di-$(C_1-C_4)$-alkylamino, $(C_1-C_8)$-alkoxy which may be substituted by hydroxyl, $(C_1-C_4)$-alkoxy, $(C_3-C_7)$-cycloalkyl, $(C_2-C_4)$-alkenyl, $(C_6-C_{10})$-aryl, 5- or 6-membered heteroaryl having up to three heteroatoms from the group consisting of N, O and/or S, $(C_6-C_{10})$-aryloxy, halogen, cyano, $(C_1-C_4)$-alkoxycarbonyl, $(C_1-C_4)$-alkanoyloxy, amino or mono- or di-$(C_1-C_4)$-alkylamino, hydrogen, hydroxyl, halogen, nitro, cyano or —NH—C(O)—$R^7$, in which R⁷ represents $(C_1-C_8)$-alkyl which may be substituted by hydroxyl or $(C_1-C_4)$-alkoxy, $(C_3-C_7)$-cycloalkyl or $(C_6-C_{10})$-aryl which may be substituted up to three times by, independently of one another, by halogen, nitro, $(C_1-C_4)$-alkoxy, carboxyl, $(C_1-C_4)$-alkoxycarbonyl or mono- or di-$(C_1-C_4)$-alkylamino, or R¹ and R² are attached to adjacent phenyl ring atoms and, together with the two ring carbon atoms, form a 5- to 7-membered saturated or partially unsaturated heterocycle having one or two heteroatoms from the group consisting of N, O and/or S which may be substituted by $(C_1-C_4)$-alkyl or oxo, R⁴ represents hydrogen, $(C_1-C_8)$-alkyl which may be substituted by hydroxyl, $(C_1-C_4)$-alkoxy, $(C_3-C_7)$-cycloalkyl, $(C_6-C_{10})$-aryl, 5- or 6-membered saturated or partially unsaturated heterocyclyl having up to three heteroatoms from the group consisting of N, O and/or S or 5- to 10-membered heteroaryl having up to three heteroatoms from the group consisting of N, O and/or S, or $(C_3-C_7)$-cycloalkyl which may be substituted by hydroxyl or $(C_1-C_8)$-alkyl, R⁵ represents $(C_1-C_4)$-alkyl or $(C_1-C_4)$-alkoxy which may be mono- or disubstituted, independently of one another, by hydroxyl, $(C_1-C_4)$-alkoxy, $(C_3-C_7)$-cycloalkyl, $(C_6-C_{10})$-aryl or 5- to 10-membered heteroaryl having up to three heteroatoms from the group consisting of N, O and/or S, where aryl and heteroaryl for their part may be substituted by halogen, $(C_1-C_4)$-alkyl, $(C_1-C_4)$-alkoxy, amino, mono- or di-$(C_1-C_4)$-alkylamino, nitro, cyano, trifluoromethyl or hydroxyl, or $(C_2-C_4)$-alkenyl, R⁶ represents $(C_1-C_8)$-alkyl which may be substituted by hydroxyl, $(C_1-C_4)$-alkoxy, $(C_3-C_7)$-cycloalkyl, $(C_2-C_4)$-alkenyl, —CO—O—R⁸, $(C_6-C_{10})$-aryl or 5- to 10-membered heteroaryl having up to three heteroatoms from the group consisting of N, O and/or S where aryl and heteroaryl for their part may be substituted by halogen, $(C_1-C_4)$-alkyl, $(C_1-C_4)$-alkoxy, amino, mono- or di-$(C_1-C_4)$-alkylamino, nitro, cyano, trifluoromethyl or hydroxyl, $(C_3-C_7)$-cycloalkyl or —CO—O—R⁸, in which R⁸ represents hydrogen, $(C_1-C_8)$-alkyl which may be substituted by hydroxyl or $(C_1-C_4)$-alkoxy, $(C_3-C_7)$-cycloalkyl or $(C_6-C_{10})$-aryl which may be substituted up to three times, independently of one another, by halogen, nitro, $(C_1-C_4)$-alkoxy, carboxyl, $(C_1-C_4)$-alkoxycarbonyl or mono- or di-$(C_1-C_4)$-alkylamino, or R⁵ and R⁶ together with the carbon atom to which they are attached form a 3- to 7-membered saturated or partially unsaturated ring which may contain one or two heteroatoms from the group consisting of N, O and/or S in the ring and which may be mono- to trisubstituted, independently of one another, by oxo, fluorine, chlorine, bromine, hydroxyl, $(C_1-C_6)$-alkyl or $(C_1-C_6)$-alkoxy, and their salts, hydrates, hydrates of the salts and solvates.

Depending on the substitution pattern, the compounds of the formula (I) can exist in stereoisomeric forms which are either like image and mirror image (enantiomers) or not like image and mirror image (diastereomers). The invention relates both to the enantiomers or diastereomers and to their respective mixtures. The racemic forms, like the diastereomers, can be separated in a known manner into the stereoisomerically uniform components. Likewise, the present invention also relates to the tautomers of the compounds of the formula (I).

Salts of the compounds of the formula (I) can be physiologically acceptable salts of the compounds according to the invention with mineral acids, carboxylic acids, or sulfonic acids. Particular preference is given, for example, to salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, trifluoroacetic acid, acetic acid, propionic acid, lactic acid, tartaric acid, citric acid, fumaric acid, maleic acid or benzoic acid.

Salts which may be mentioned include salts with customary bases, such as, for example, alkali metal salts (for example sodium salts or potassium salts), alkaline earth metal salts (for example calcium salts or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine, 1-ephenamine or methylpiperidine.

According to the invention, hydrates or solvates are those forms of the compounds of the formula (I) which, in solid or liquid state, form, by hydration with water or coordination with solvent molecules, a molecule compound or a complex. Examples of hydrates are sesquihydrates, monohydrates, dihydrates or trihydrates. Likewise, the hydrates or solvates of salts of the compounds according to the invention are also suitable.

Moreover, the invention also includes prodrugs of the compounds according to the invention. According to the invention, prodrugs are forms of compounds of the formula (I) which for their part may be biologically active or inactive, but which can be converted under physiological conditions (for example metabolically or solvolytically) into the corresponding biologically active form.

In the context of the present invention, the substituents have, unless defined otherwise, the following meanings:

Halogen generally represents fluorine, chlorine, bromine or iodine. Preference is given to fluorine, chlorine or bromine. Very particularly preferred are fluorine or chlorine.

$(C_1-C_8)$-Alkyl, $(C_1-C_6)$-alkyl and $(C_1-C_4)$-alkyl generally represent a straight-chain or branched alkyl radical having 1 to 8, 1 to 6 and 1 to 4 carbon atoms, respectively. Preference is given to a straight-chain or branched alkyl radical having 1 to 6 carbon atoms. Particular preference is given to a straight-chain or branched alkyl radical having 1 to 4 carbon atoms. Examples which may be mentioned are: methyl, ethyl, n-propyl, isopropyl, n-butyl, sec-butyl, isobutyl and tert-butyl.

$(C_2-C_4)$-Alkenyl generally represents a straight-chain or branched alkyl radical having 2 to 4 carbon atoms. Examples which may be mentioned are: vinyl, allyl, isopropenyl and n-but-2-en-1-yl.

$(C_2-C_4)$-Alkynyl generally represents a straight-chain or branched alkynyl radical having 2 to 4 carbon atoms. Examples which may be mentioned are: ethynyl, n-prop-2-yn-1-yl and n-but-2-yn-1-yl.

$(C_1-C_8)$-Alkoxy, $(C_1-C_6)$-alkoxy and $(C_1-C_4)$-alkoxy generally represent a straight-chain or branched alkoxy radical having 1 to 8, 1 to 6 and 1 to 4 carbon atoms, respectively. Preference is given to a straight-chain or branched alkoxy radical having 1 to 6 carbon atoms. Particular preference is given to a straight-chain or branched alkoxy radical having 1 to 4 carbon atoms. Examples which may be mentioned are: methoxy, ethoxy, n-propoxy, isopropoxy, n-butoxy, sec-butoxy, isobutoxy, tert-butoxy.

$(C_1-C_4)$-Alkoxycarbonyl generally represents a straight-chain or branched alkoxy radical having 1 to 4 carbon atoms which is attached via a carbonyl group. Examples which may be mentioned are: methoxycarbonyl, ethoxycarbonyl, n-propoxycarbonyl, isopropoxycarbonyl and t-butoxycarbonyl.

$(C_1–C_4)$-Alkanoyloxy generally represents a straight-chain or branched alkyl radical having 1 to 4 carbon atoms which carries a doubly attached oxygen atom in the 1-position and is attached in the 1-position via a further oxygen atom. Examples which may be mentioned are: acetoxy, propionoxy, n-butyroxy and i-butyroxy.

In the context of the invention, mono- or di-$(C_1–C_4)$-alkylamino represents an amino group having one or two identical or different straight-chain or branched alkyl substituents each having 1 to 4 carbon atoms. Examples which may be mentioned are: methylamino, ethylamino, n-propylamino, isopropylamino, t-butylamino, N,N-dimethylamino, N,N-diethylamino, N-ethyl-N-methylamino, N-methyl-N-n-propylamino, N-isopropyl-N-n-propylamino and N-t-butyl-N-methylamino.

$(C_3–C_7)$-Cycloalkyl and $(C_3–C_6)$-cycloalkyl generally represent a cyclic alkyl radical having 3 to 7 and 3 to 6 carbon atoms, respectively. Preference is given to cyclic alkyl radicals having 3 to 6 carbon atoms. Examples which may be mentioned are: cyclopropyl, cyclobutyl, cyclopentyl or cyclohexyl.

$(C_6–C_{10})$-Aryl generally represents an aromatic radical having 6 to 10 carbon atoms. Preferred aryl radicals are phenyl and naphthyl.

$(C_6-_{10})$-Aryloxy generally represents an aromatic radical as defined above which is attached via an oxygen atom.

5- to 10-membered heteroaryl having up to 3 heteroatoms from the group consisting of N, O and/or S generally represents a mono- or bicyclic, optionally benzo-fused heteroaromatic which is attached via a ring carbon atom of the heteroaromatic, if appropriate also via a ring nitrogen atom of the heteroaromatic. Examples which may be mentioned are: pyridyl, pyrimidyl, pyridazinyl, pyrazinyl, thienyl, furyl, pyrrolyl, pyrazolyl, imidazolyl, triazolyl, thiazolyl, oxazolyl, oxdiazolyl, isoxazolyl, benzofuranyl, benzothienyl or benzimidazolyl. The corresponding heteroaromatics having fewer heteroatoms, such as, for example, those having one or 2 heteroatoms from the group consisting of N, O and/or S, or those having a smaller ring size, such as, for example, 5- or 6-membered heteroaryl, are derived analogously from this definition. In general, preference is given to 5- or 6-membered aromatic heterocycles having one or 2 heteroatoms from the group consisting of N, O and/or S. Examples which may be mentioned are: pyridyl, pyrimidyl, pyridazinyl, furyl, imidazolyl or thienyl.

5- to 7-membered heterocycle generally represents a saturated or partially unsaturated, optionally benzo-fused heterocycle having up to 3 heteroatoms from the group consisting of N, O and/or S. Examples which may be mentioned are: tetrahydrofuryl, pyrrolidinyl, pyrrolinyl, dihydropyridinyl, piperidinyl, piperazinyl, morpholinyl, thiomorpholinyl, hexahydropyranyl. The corresponding heterocycles having fewer heteroatoms, such as, for example, one or 2 heteroatoms from the group consisting of N, O and/or S, or a smaller ring size, such as, for example, 5- or 6-membered heterocyclyl, are derived analogously from this definition. Preference is given to saturated heterocycles having up to 2 heteroatoms from the group consisting of N, O and/or S, in particular piperidinyl, piperazinyl, morpholinyl and pyrrolidinyl.

Preference is given to compounds of the formula (I)

in which $R^1$ and $R^2$ independently of one another represent hydrogen, $(C_1–C_6)$-alkyl, $(C_1–C_6)$-alkoxy which may be substituted by hydroxyl, $(C_1–C_4)$-alkoxy, $(C_1–C_4)$-alkanoyloxy or cyclopropyl, hydrogen, hydroxyl, fluorine, chlorine, nitro or —NH—C(O)—CH$_3$ or $R^1$ and $R^2$ are attached to adjacent phenyl ring atoms and represent a group —O—CH$_2$— or —O—CH$_2$—CH$_2$—O—, $R^3$ represents hydrogen, $R^4$ represents hydrogen, $(C_1–C_4)$-alkyl which is substituted by hydroxyl, $(C_1–C_4)$-alkoxy or cyclopropyl, or cyclopropyl, $R^5$ represents $(C_1–C_4)$-alkyl which may be mono- or disubstituted, independently of one another, by $(C_3–C_6)$-cycloalkyl, phenyl, which for its part may be substituted by fluorine, trifluoromethyl or $(C_1–C_4)$-alkoxy, pyridyl, furyl or thienyl, or $(C_2–C_4)$-alkenyl, and $R^6$ represents $(C_1–C_4)$-alkyl or $(C_1–C_4)$-alkoxycarbonyl or $R^5$ and $R^6$ together with the carbon atom to which they are attached form a 3- to 7-membered saturated or partially unsaturated ring which may contain a heteroatom from the group consisting of N, O or S in the ring and their salts, hydrates, hydrates of the salts and solvates.

Particular preference is given to compounds of the formula (I)

in which $R^1$ represents hydrogen, chlorine, nitro, methyl, methoxy, ethoxy, n-propoxy, isopropoxy, n-butoxy, where the alkoxy radicals for their part may be substituted by hydroxyl, methoxy, ethoxy, n-propoxy, isopropoxy, n-butoxy, —O—C(O)—CH$_3$ or cyclopropyl, or —NH—C(O)—CH$_3$, $R^2$ represents hydrogen or $R^1$ and $R^2$ are attached to adjacent phenyl ring atoms and represent a group —O—CH$_2$—O—, $R^3$ represents hydrogen, $R^4$ represents hydrogen, methyl, ethyl, n-propyl, isopropyl, n-butyl, where the alkyl radicals for their part may be substituted by hydroxyl, methoxy, ethoxy, n-propoxy, isopropoxy, n-butoxy or cyclopropyl, or cyclopropyl, $R^5$ represents methyl, ethyl, n-propyl, isopropyl, n-butyl, where the alkyl radicals for their part may be mono- or disubstituted, independently of one another, by cyclopropyl, phenyl, which for its part may be substituted by fluorine, trifluoromethyl or methoxy, pyridyl, furyl or thienyl, ethenyl, propenyl or butenyl and $R^6$ represents methyl, ethyl, n-propyl, isopropyl, n-butyl, methoxycarbonyl, ethoxycarbonyl, n-propoxycarbonyl, isopropoxycarbonyl, n-butoxycarbonyl or isobutoxycarbonyl or $R^5$ and $R^6$ together with the carbon atom to which they are attached form a cyclopropyl, cyclobutyl, cyclopentyl or cyclohexyl ring and their salts, hydrates, hydrates of the salts and solvates.

Particular preference is likewise given to compounds of the formula (I) in which $R^1$ and $R^2$ are attached to adjacent phenyl ring atoms located in the para and meta position to the point of attachment of the pyridine ring and represent a group —O—CH$_2$—O—.

The general or preferred radical definitions or illustrations given above can be combined with one another as desired, i.e. including combinations between the respective ranges and preferred ranges. They apply both to the end products and, correspondingly, to precursors and intermediates.

The present invention furthermore relates to a process for preparing the compounds of the formula (I), characterized in that either

[A] Compounds of the Formula (II)

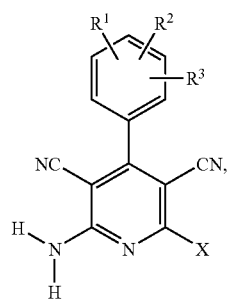

(II)

in which
$R^1$, $R^2$ and $R^3$ are as defined above and X represents a suitable leaving group, such as, for example, chlorine, bromine, methylthio or phenylthio, are initially reacted with ethyl malonamide (III)

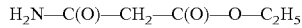

H$_2$N—C(O)—CH$_2$—C(O)—O—C$_2$H$_5$ (III)

to give compounds of the formula (IV)

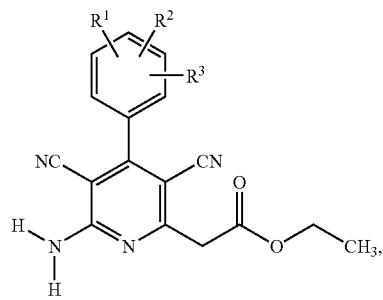

(IV)

in which
$R^1$, $R^2$ and $R^3$ are as defined above, and then with compounds of the formula (V)

R$^5$—Y (V)

in which
$R^5$ is as defined above and Y represents a suitable leaving group, such as, for example, chlorine, bromine or iodine, to give compounds of the formula (I)

in which
$R^1$, $R^2$, $R^3$, $R^4$ and $R^5$ are as defined above and $R^6$ represents a radical —C(O)—O—C$_2$H$_5$, and, if appropriate, subsequently with compounds of the formula (VI)

R$^8$—OH (VI)

in which $R^8$ is as defined above to give compounds of the formula (I)

in which
$R^6$ represents a radical —C(O)—O—R$^8$ and $R^1$, $R^2$, $R^3$, $R^4$, $R^5$ and $R^8$ are as defined above, or

[B] Compounds of the Formula (II)
are reacted in an inert solvent in the presence of a catalyst with Grignard compounds of the formula (VII)

(VII)

in which
$R^5$ and $R^6$ are as defined above to give compounds of the formula (I)

in which
$R^1$, $R^2$, $R^3$, $R^5$ and $R^6$ are as defined above and $R^4$ represents hydrogen, and, if appropriate, subsequently with compounds of the formula (VIII)

R$^4$—Y' (VIII)

in which
$R^4$ is as defined above and Y' has the meaning of Y.

The process according to the invention can be illustrated in an exemplary manner by the formula scheme below:

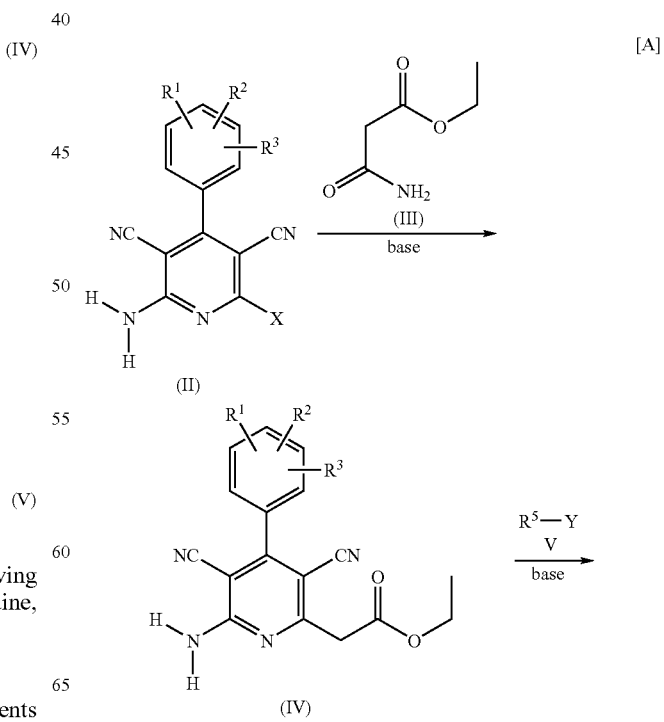

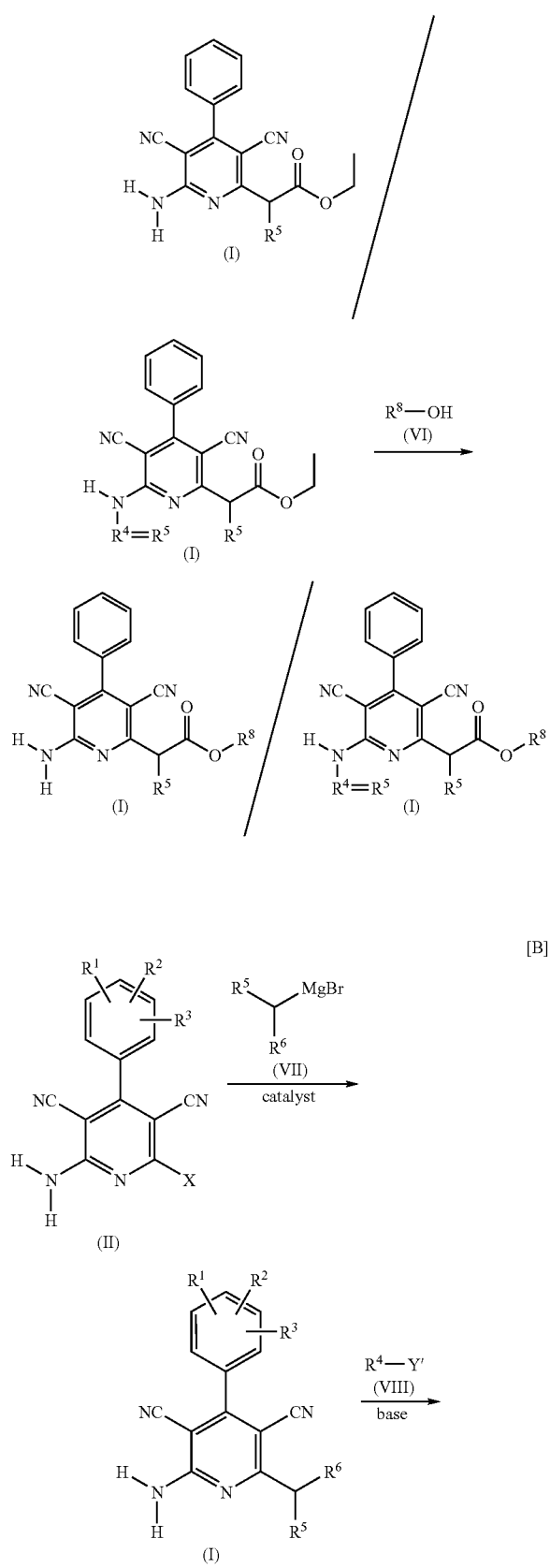

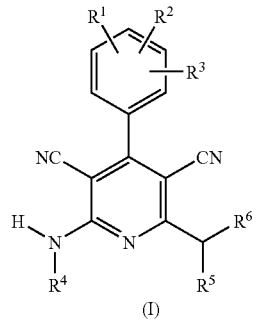

Suitable solvents for the first reaction step [A]: (II)+(III) →(IV) are organic solvents which do not change under the reaction conditions. These include alcohols, such as methanol, ethanol and isopropanol, ketones, such as acetone and methyl ethyl ketone, acyclic and cyclic ethers, such as diethyl ether and tetrahydrofuran, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulfoxide (DMSO). It is also possible to use mixtures of the solvents mentioned above. Preference is given to DMF.

Suitable bases are the customary inorganic or organic bases. These include alkali metal hydroxides, such as, for example, sodium hydroxide or potassium hydroxide, alkali metal carbonates, such as sodium carbonate or potassium carbonate, or sodium bicarbonate or potassium bicarbonate, potassium tert-butoxide, sodium hydroxide, amides, such as sodium amide, lithium bis(trimethylsilyl)amide or lithium diisopropylamide, organometallic compounds, such as butyllithium or phenyllithium, or else the sodium or potassium salt of the respective compound of the general formula (VI) itself. Preference is given to potassium tert-butoxide and potassium carbonate.

Here, the base can be employed in a ratio of from 1 to 10 mol, preferably in a ratio of from 1 to 5 mol, in particular in a ratio of from 1 to 4 mol, of base per mole of the compound (II).

The reaction is generally carried out in a temperature range of from −78° C. to +150° C., preferably in the range from +20° C. to +80° C., in particular at from +20° C. to +60° C.

The reaction can be carried out under atmospheric, elevated or reduced pressure, for example in the range of from 0.5 to 5 bar. In general, the reaction is carried out at atmospheric pressure.

In general, the reaction is carried out using an excess of compounds (III), preferably in a ratio of from 1.5 to 8 mol of the compound (III) per mole of the compound (II).

In the second process step [A]: (IV)+(V)→(I), under the reaction conditions a product mixture may be formed where, in addition to the carbon atom in the α-position to the ester function, the nitrogen atom of the aminopyridine unit is also alkylated. This gives compounds of the formula (I) in which the substituent $R^4$ either represents hydrogen or has the meaning of $R^5$. The different products can be separated chromatographically.

Suitable solvents for this reaction are organic solvents which are inert under the reaction conditions. These include ketones, such as acetone and methyl ethyl ketone, acyclic and cyclic ethers, such as diethyl ether, 1,2-dimethoxyethane or tetrahydro-furan, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulfoxide (DMSO). It is also possible to use mixtures of the solvents mentioned above. Preference is given to DMF.

Suitable bases are the customary inorganic or organic bases. These include alkali metal hydroxides, such as, for example, sodium hydroxide or potassium hydroxide, alkali metal carbonates, such as sodium carbonate or potassium carbonate or sodium bicarbonate or potassium bicarbonate, potassium tert-butoxide, sodium hydride, amides, such as sodium amide, lithium bis(trimethylsilyl)amide or lithium diisopropylamide, organometallic compounds, such as butyllithium or phenyllithium, amines, such as triethylamine or pyridine, or else the sodium or potassium salt of the respective compound of the general formula (IV) itself. Preference is given to potassium tert-butoxide and potassium carbonate.

Here, the base can be employed in a ratio of from 1 to 10 mol, preferably in a ratio of from 1 to 5 mol, in particular in a ratio of from 1 to 4 mol, of base per mole of the compound (IV).

The reaction is generally carried out in a temperature range of from −78° C. to +120° C., preferably in a range of from +20° C. to +100° C., in particular at from +20° C. to +80° C.

The reaction can be carried out at atmospheric, elevated or reduced pressure, for example in the range from 0.5 to 5 bar. In general, the reaction is carried out at atmospheric pressure.

The reaction is generally carried out using an equivalent amount or else an excess of compound (V), preferably in a ratio of from 1 to 5 mol of the compound (V) per mole of the compound (IV). Suitable solvents for the third process step [A]: (I)+(VI)→(I), which is carried out, if appropriate, are organic solvents which are inert under the reaction conditions. The reaction is preferably carried out using an excess of alcohol (VI) as solvent.

The reaction is generally carried out in a temperature range of from −78° C. to +120° C., preferably in a range of from +20° C. to +100° C., in particular at from +30° C. to +80° C.

The reaction can be carried out at atmospheric, elevated or reduced pressure, for example in the range from 0.5 to 5 bar. In general, the reaction is carried out at atmospheric pressure.

The reaction is generally carried out using a large an excess of compound (VI), which simultaneously serves as reaction solvent.

The reaction is generally carried out in the presence of a basic catalyst. Suitable basic catalysts are the customary inorganic or organic bases. These include alkali metal hydroxides, such as, for example, sodium hydroxide or potassium hydroxide, alkali metal carbonates, such as sodium carbonate or potassium carbonate or sodium bicarbonate or potassium bicarbonate, potassium tert-butoxide, sodium hydride, amides, such as sodium amide, lithium bis(trimethylsilyl)amide or lithium diisopropylamide, organometallic compounds, such as butyllithium or phenyllithium, amines, such as triethylamine or pyridine, or else the sodium or potassium salt of the respective compound of the general formula (VI) itself. Other suitable basic catalysts are basic reducing agents, such as, for example, sodium borohydride or potassium borohydride. Preference is given to sodium borohydride, potassium tert-butoxide and potassium carbonate.

Suitable solvents for the first reaction step [B]: (II)+(VII)→(I) are organic solvents which are inert under the reaction conditions. These include acyclic and cyclic ethers, such as diethyl ether, 1,2-dimethoxyethane or tetrahydrofuran, hydrocarbons, such as benzene, xylene, toluene, hexane or cyclohexane, chlorinated hydrocarbons, such as dichloromethane, chlorobenzene or dichloroethane, or other solvents, such as pyridine or dimethyl sulfoxide (DMSO). It is also possible to use mixtures of the solvents mentioned above. Preference is given to diethyl ether or tetrahydrofuran.

The reaction is generally carried out in a temperature range of from −78° C. to +120° C., preferably in a range of from +20° C. to +60° C., in particular at from +40° C. to +60° C.

The reaction can be carried out at atmospheric, elevated or reduced pressure, for example in the range from 0.5 to 5 bar. In general, the reaction is carried out at atmospheric pressure.

Suitable catalysts are nickel(II) complexes, such as, for example, 1,3-bis(diphenyl-phosphino)propanedichloronickel(II) or bis(triphenylphosphine)dichloronickel (II) (see Chemistry Letters 1447–1450 (1979)). The catalyst is employed in a ratio of from 0.001 to 0.1 mol, preferably in a ratio of from 0.03 to 0.1 mol, of catalyst per mole of the compound (II).

The reaction is generally carried out using an equivalent amount or using an excess of compound (VII), preferably in a ratio of from 2 to 8 mol of compound (VII), particularly preferably in a ratio of from 2 to 4 mol of the compound (VII), per mole of the compound (II).

Suitable solvents for the second reaction step [B]: (I)+(VIII)→(I), which is carried out, if appropriate, are organic solvents which are inert under the reaction conditions. These include ketones, such as acetone and methyl ethyl ketone, acyclic and cyclic ethers, such as diethyl ether, 1,2-dimethoxyethane or tetrahydrofuran, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulfoxide (DMSO). It is also possible to use mixtures of the solvents mentioned above. Preference is given to DMF.

Suitable bases are the customary inorganic or organic bases. These include alkali metal hydroxides, for example, sodium hydroxide or potassium hydroxide, alkali metal carbonates, such as sodium carbonate or potassium carbonate or sodium bicarbonate or potassium bicarbonate, potassium tert-butoxide, sodium hydride, amides, such as sodium amide, lithium bis(trimethylsilyl)amide or lithium diisopropylamide, organometallic compounds, such as butyllithium or phenyllithium, amines, such as triethylamine or pyridine, or else the sodium or potassium salt of the respective compound of the general formula (IV) itself. Preference is given to potassium tert-butoxide and potassium carbonate.

Here, the base can be employed in a ratio of from 1 to 10 mol, preferably in a ratio of from 1 to 5 mol, in particular in a ratio of from 1 to 4 mol, of base per mole of the compound (I).

The reaction is generally carried out in a temperature range of from −78° C. to +120° C., preferably in a range of from +20° C. to +100° C., in particular at from +20° C. to +80° C.

The reaction can be carried out at atmospheric, elevated or reduced pressure, for example in the range from 0.5 to 5 bar. In general, the reaction is carried out at atmospheric pressure.

In general, the reaction is carried out using an equivalent amount or using an excess of compound (VIII), preferably in a ratio of from 1 to 5 mol of the compound (VIII) per mole of the compound (I).

The compounds of the formula (II) are known to the person skilled in the art or can be prepared analogously to methods known from the literature [see, for example, J. M. Quintela, J. L. Soto, Anales de Quimica 79, 368–372 (1983)].

The compounds of the formulae (III), (V), (VI) and (VIII) are commercially available, known to the person skilled in the art or preparable by methods known from the literature.

The compounds of the formula (VII) are known to the person skilled in the art or can be prepared analogously to methods known from the literature [see, for example, Organikum, 18. corr. ed., Deutscher Verlag der Wissenschaften, Berlin 1990, page 499].

Surprisingly, the compounds of the formula (I) have an unforeseeable useful pharmacological activity spectrum and are therefore suitable in particular for the prophylaxis and/or treatment of disorders.

The compounds of the formula (I) are suitable for the prophylaxis and/or treatment of a number of disorders, such as, for example, in particular disorders of the cardiovascular system (cardiovascular disorders).

In the context of the present invention, cardiovascular disorders are to be understood as meaning, in particular, for example the following disorders: coronary heart disease, hypertension (high blood pressure), restenosis after balloon dilation of peripheral blood vessels, arteriosclerosis, tachycardia, arrhythmias, peripheral vascular disorders and cardiovascular disorders, stable and unstable angina pectoris and atrial fibrillation.

The compounds of the formula (I) are furthermore also particularly suitable, for example, for reducing the size of the myocardial area affected by an infarct.

The compounds of the formula (I) are furthermore particularly suitable, for example, for the prophylaxis and/or treatment of thromboembolic disorders and ischemias, such as myocardial infarction, stroke and transitory ischemic attacks.

Finally, the compounds of the formula (I) are in particular also suitable, for example, for the prophylaxis and/or treatment of diabetes, in particular diabetes mellitus.

The present invention also relates to the use of the compounds of the formula (I) for preparing medicaments and pharmaceutical compositions for the prophylaxis and/or treatment of the clinical pictures mentioned above.

The present invention furthermore relates to a method for the prophylaxis and/or treatment of the clinical pictures mentioned above using the compounds of the formula (I).

The pharmaceutical activity of the compounds of the formula (I) mentioned above can be explained in particular by their action as selective ligands on A1 adenosine receptors.

In the context of the present invention, adenosine receptor ligands are referred to as being "selective" if, firstly, they are clearly active on one or more adenosine receptor subtypes and, secondly, the activity that can be observed on one or more other adenosine receptor subtypes is considerably weaker, if present at all, where, with respect to the test methods for selectivity of action, reference is made to the test methods described in Section A. II.

One advantage of the compounds of the formula (I) according to the invention is that they are more selective than adenosine receptor ligands of the prior art.

The receptor selectivity can be determined by biochemical measurement of the intracellular messenger cAMP in the transfected cells which specifically only express one subtype of the adenosine receptors. In the case of A1 agonists (coupling preferably via Gi proteins) a decrease of the intracellular cAMP content is noticed under conditions in which the intracellular cAMP concentration would be significantly increased by stimulating adenylate cyclase. In contrast, in the case of A1 antagonists, an increase of the intracellular cAMP concentration is observed after comparable prestimulation of adenylate cyclase plus stimulation with adenosine or adenosine-like substances.

Thus, compounds of the formula (I) which bind selectively to adenosine A1 receptors are preferably suitable for myocard protection and for the prophylaxis and/or treatment of tachycardia, atrial arrhythmia, cardiac insufficiency, myocardial infarction, acute kidney failure, diabetes, pain and for wound healing.

The subject matter of the present invention furthermore includes medicaments and pharmaceutical compositions comprising at least one compound of the formula (I), preferably together with one or more pharmacologically acceptable auxiliaries or carriers, and their use for the purposes mentioned above.

Suitable for administering the compounds of the formula (I) are all customary administration forms, i.e. oral, parenteral, inhalative, nasal, sublingual, rectal, local, such as, for example, in the case of implants or stents, or external, such as, for example, transdermal. In the case of parenteral administration, particular mention may be made of intravenous, intramuscular and subcutaneous administration, for example as a subcutaneous depot. Particular preference is given to oral administration.

Here, the active compounds can be administered on their own or in the form of preparations. Suitable preparations for oral administration are inter alia tablets, capsules, pellets, sugar-coated tablets, pills, granules, solid and liquid aerosols, syrups, emulsions, suspensions and solutions. Here, the active compound has to be present in such a quantity that a therapeutic effect is obtained. In general, the active compound can be present in a concentration of from 0.1 to 100% by weight, in particular from 0.5 to 90% by weight, preferably from 5 to 80% by weight. i.e. the active compound should be present in quantities sufficient to achieve the dosage range mentioned.

To this end, the active compounds can be converted in a manner known per se to the customary preparations. This is achieved using inert nontoxic pharmaceutically suitable carriers, auxiliaries, solvents, vehicles, emulsifiers and/or dispersants.

Auxiliaries which may be mentioned are, for example: water, nontoxic organic solvents, such as, for example, paraffins, vegetable oils (for example sesame oil), alcohols (for example ethanol, glycerol), glycols (for example polyethylene glycol), solid carriers, such as natural or synthetic ground minerals (for example talc or silicates), sugars (for example lactose), emulsifiers, dispersants (for example polyvinylpyrrolidone) and glidants (for example magnesium sulfate).

In the case of oral administration, tablets may, of course, also contain additives such as sodium citrate, together with adjuvants such as starch, gelatin and the like. Aqueous preparations for oral administration may furthermore be admixed with flavor enhancers or colorants.

In general, it has been found to be advantageous to administer, in the case of parenteral administration, quantities of from about 0.1 to about 10 000 µg/kg, preferably from about 1 to about 1000 µg/kg, in particular from about 1 µg/kg to about 100 µg/kg, of body weight, to obtain effective results. In the case of oral administration, the quantity is from about 0.1 to about 10 mg/kg, preferably from about 0.5 to about 5 mg/kg, in particular from about 1 to about 4 mg/kg, of body weight.

In spite of this, it may still be required, depending on body weight, administration route, individual response to the active compound, the type of preparation and the time or interval at which administration takes place, to deviate from the quantities mentioned.

The present invention is illustrated by the following examples, which do not restrict the invention in any way.

A. Assessing Physiological Activity

I. Detecting the Cardiovascular Effect

Langendorff Heart of the Rat:

After the thorax has been opened, the heart is rapidly removed from anesthetized rats and introduced into a conventional Langendorff apparatus. The coronary arteries are perfused at constant volume (10 ml/min), and the resulting perfusion pressure is recorded by way of an appropriate pressure sensor. In this set-up, a decrease in the perfusion pressure corresponds to a relaxation of the coronary arteries. At the same time, the pressure which the heart develops during each contraction is measured by way of a balloon, which has been introduced into the left ventricle, and a second pressure sensor. The frequency of the heart, which is beating in isolation, is calculated from the number of contractions per time unit.

II. Assessing the Receptor Selectivity a) Adenosine A1, A2a, A2b and A3 Receptor Selectivity Cells of the CHO (Chinese Hamster Ovary) permanent cell line are transfected stably with the cDNA for the adenosine receptor subtypes A1, A2a, A2b and A3. The binding of the substances to the A2a or A2b receptor subtypes is determined by measuring the intracellular cAMP content in these cells using a conventional radioimmunological assay (cAMP RIA).

When the substances act as agonists, the binding of the substances is expressed as an increase in the intracellular content of cAMP. The adenosine-analogous compound NECA (5-N-ethylcarboxamido-adenosine), which binds all adenosine receptor subtypes with high affinity but not selectively and possesses an agonistic effect, is used as the reference compound in these experiments (Klotz, K. N., Hessling, J., Hegler, J., Owman, C., Kull, B., Fredholm, B. B., Lohse, M. J., Comparative pharmacology of human adenosine receptor subtypes—characterization of stably transfected receptors in CHO cells, Naunyn Schmiedebergs Arch Pharmacol, 357 (1998), 1–9).

The adenosine receptors A1 and A3 are coupled to a Giα1 protein, i.e. stimulation of these receptors leads to inhibition of the adenylate cyclase and consequently to a lowering of the intracellular cAMP level. In order to identify A1/A3 receptor agonists, the adenylate cyclase is stimulated with forskolin. However, an additional stimulation of the A1/A3 receptors inhibits the adenylate cyclase, which means that A1/A3 receptor agonists can be detected by a comparatively low content of cAMP in the cell.

In order to detect an antagonistic effect on adenosine receptors, the recombinant cells which are transfected with the corresponding receptor are prestimulated with NECA and the effect of the substances on reducing the intracellular content of cAMP occasioned by this prestimulation is investigated. XAC (xanthine amine congener), which binds to all adenosine receptor subtypes with high affinity but not selectively and possesses an antagonistic effect, is used as the reference compound in these experiments (Müller, C. E., Stein, B., Adenosine receptor antagonists: structures and potential therapeutic applications, Current Pharmaceutical Design, 2 (1996) 501–530).

b) Adenosine A1, A2a, A2b Receptor Selectivity

Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of Gs proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance test screening:

The stock cultures are grown, at 37° C. and under 5% $CO_2$, in DMEM/F12 medium containing 10% FCS (fetal calf serum) and in each case split 1:10 after 2–3 days. The test cultures are seeded in 384-well plates at the rate of from 1 000 to 3 000 cells per well and grown at 37° C. for approx. 48 hours. The medium is then replaced with a physiological sodium chloride solution (130 mM NaCl, 5 mM KCL, 2 mM $CaCl_2$, 20 mM HEPES, 1 mM $MgCl_2.6H_2O$, 5 mM $NaHCO_3$, pH 7.4). The substances, which are dissolved in DMSO, are diluted 1:10 three times with this physiological sodium chloride solution and pipetted into the test cultures (maximum final concentration of DMSO in the test mixture: 0.5%). In this way, final substance concentrations of, for example, from 5 µM to 5 nM are obtained. 10 minutes later, forskolin is added to the A1 cells and all the cultures are subsequently incubated at 37° C. for 4 hours. After that, 35 µl of a solution which is composed of 50% lysis reagent (30mM disodium hydrogenphosphate, 10% glycerol, 3% TritonX100, 25 mM TrisHCl, 2 mM dithiothreitol (DTT), pH 7.8) and 50% luciferase substrate solution (2.5 mM ATP, 0.5 mM luciferin, 0.1 mM coenzyme A, 10 mM tricine, 1.35 mM $MgSO_4$, 15 mM DTT, pH 7.8) are added to the test cultures, the plates are shaken for approx. 1 minute and the luciferase activity is measured using a camera system.

B. WORKING EXAMPLES

Abbreviations Used:

| | |
|---|---|
| eq. | equivalents |
| DMF | dimethylformamide |
| DMSO | dimethyl sulfoxide |
| HPLC | high pressure, high performance liquid chromatography |
| NMR | nuclear magnetic resonance spectroscopy |
| RP | reversed phase |
| THF | tetrahydrofuran |

Example 1

Ethyl 2-[6-amino-4-(1,3-benzodioxol-5-yl)-3,5-dicyano-2-pyridinyl]propionate Step 1

Ethyl[6-amino-4-(1,3-benzodioxol-5-yl)-3,5-dicyano-2-pyridinyl]acetate

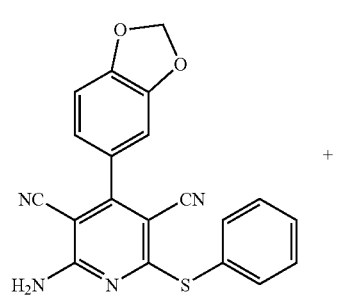

+

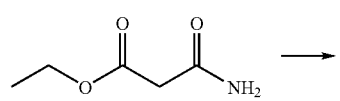

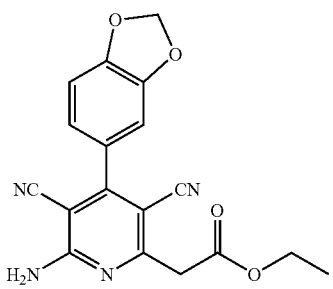

2-Amino-4-(1,3-benzodioxol-5-yl)-6-(phenylsulfanyl)-3,5-dicyanopyridine (5.00 g, 13.43 mmol) [preparation analogously to J. M. Quintela, J. L. Soto, Anales de Quimica 79, 368–372 (1983)] is initially charged with ethyl malonamide (4.23 g, 23.22 mmol) in absolute DMF (30 ml) under an atmosphere of argon. Potassium tert-butoxide (3.01 g, 26.85 mmol) is added, and the solution is then stirred at room temperature for 22 hours. The mixture is poured into water (300 ml). The mixture is then extracted three times with ethyl acetate (300 ml each) and the combined organic phases are dried over magnesium sulfate, filtered and concentrated to about 100 ml. The precipitated crystals are filtered off with suction.

Yield: 3.5 g (74% of theory)

$^1$H-NMR (200 MHz, DMSO-$d_6$): δ=1.20 (t, 3H), 3.89 (s, 2H), 4.13 (q, 2H), 6.16 (s, 2H), 7.01–7.17 (m, 3H), 8.00 (bs, 2H).

ESI (positive) calc. 350.33. found 351.166.

Step 2

Ethyl 2-[6-amino-4-(1,3-benzodioxol-5-yl)-3,5-dicyano-2-pyridinyl]propionate

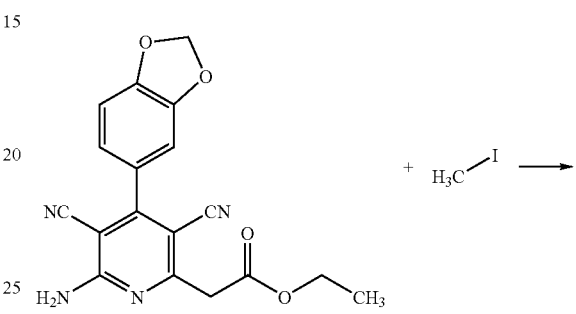

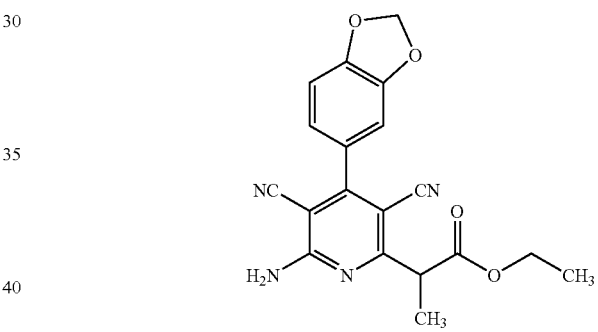

Ethyl[6-amino-4-(1,3-benzodioxol-5-yl)-3,5-dicyano-2-pyridinyl]acetate (step 1) (2.00 g, 5.71 mmol) is initially charged in 40 ml of DMF. Sodium hydride (0.37 g, 9.19 mmol) is added and the mixture is stirred for 45 minutes. Methyl iodide (0.40 ml, 6.39 mmol) is then added, the color of the yellow reaction solution turning to orange. After five hours, a further 0.2 ml of methyl iodide is added and the mixture is stirred at room temperature overnight. The mixture is poured into water (50 ml), and an emulsion is formed. The emulsion is extracted three times with ether. The combined organic phases are dried over magnesium sulfate, filtered and concentrated using a rotary evaporator. The mixture is chromatographed by RP-HPLC using an acetonitrile/water gradient. The product is obtained as a colorless solid.

Yield: 0.58 g (28% of theory)

$^1$H-NMR (200 MHz, DMSO-$d_6$): δ=1.15 (t, 3H), 1.44 (d, 3H), 4.05–4.16 (m, 3H), 6.16 (s, 2H), 7.02–7.19 (m, 3H), 7.93 (bs, 2H).

ESI (positive) calc. 364.36. found 364.997.

The corresponding ethyl- and allyl-substituted compounds from Examples 2 and 3 are prepared analogously:

Example 2

Ethyl[6-amino-4-(1,3-benzodioxol-5-yl)-3,5-dicyano-2-pyridinyl]pent-4-enoate

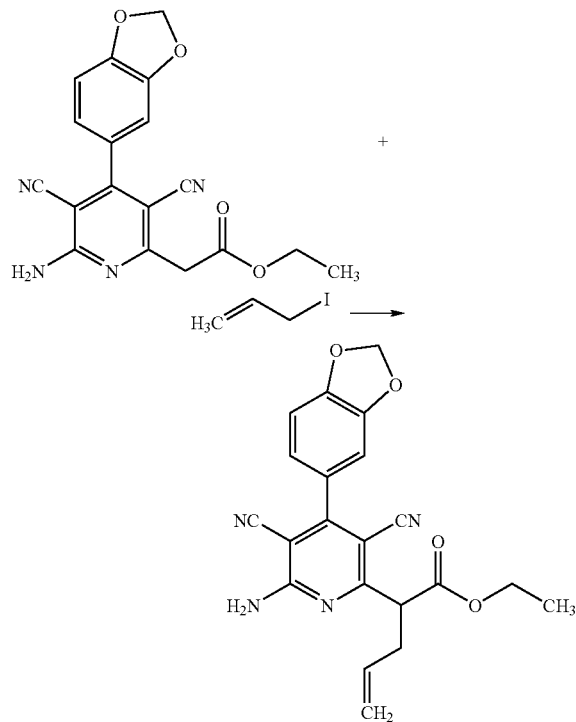

1 eq. of allyl bromide, 1.1 eq. of sodium hydride
Yield: 71% of theory
$^1$H-NMR (200 MHz, DMSO-$d_6$): δ=1.11–1.18 (t, 3H), 2.59–2.84 (m, 2H), 4.06–4.16 (m, 3H), 5.00–5.09 (m, 2H), 5.72–5.85 (m, 1H), 6.16 (s, 2H), 7.00–7.18 (m, 3H), 8.00 (bs, 2H).
ESI (positive) calc. 390.4. found [M+H] 391.1.

Example 3

Ethyl 2-[6-amino-4-(1,3-benzodioxol-5-yl)-3,5-dicyano-2-pyridinyl]butyrate

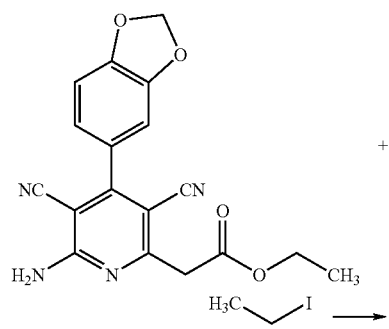

-continued

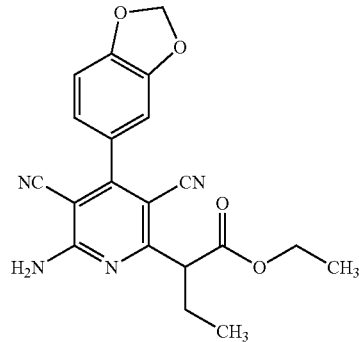

1.12 eq. ethyl iodide, 1.61 eq. sodium hydride.
Yield: 37% of theory
$^1$H-NMR (200 MHz, DMSO-$d_6$): δ=0.88 (t, 2H), 1.81–2.15 (m, 2H), 3.63 (s, 3H), 3.92–3.99 (m, 1H), 6.16 (s, 2H), 7.02–7.20 (m, 3H), 7.98 (bs, 2H).
ESI (positive) calc. 364.36. found 364.978.

Example 4

Ethyl 2-[4-(1,3-benzodioxol-5-yl)-3,5-dicyano-6-methylamino-2-pyridinyl]propionate

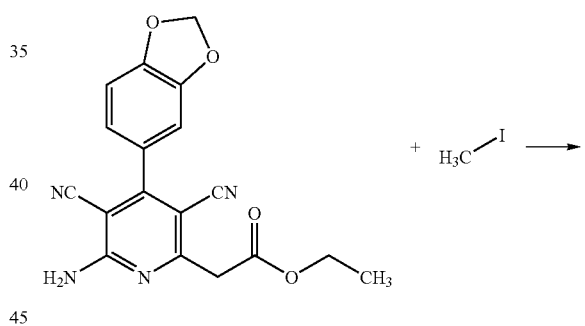

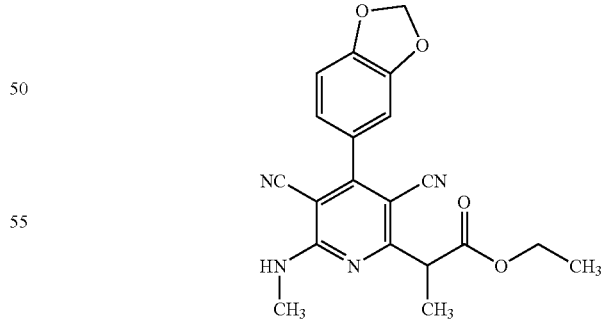

The compound is formed in the reaction of Example 1, step 2 and is isolated from the crude mixture by chromatographing the mixture using RP-HPLC and an acetonitrile/water gradient. The product is obtained as a colorless solid.
Yield: 1.1 g (51% of theory)
ESI (positive) calc. 378.39. found 378.3.

Example 5

Ethyl 2-[4-(1,3-benzodioxol-5-yl)-3,5-dicyano-6-ethylamino-2-pyridinyl]butyrate

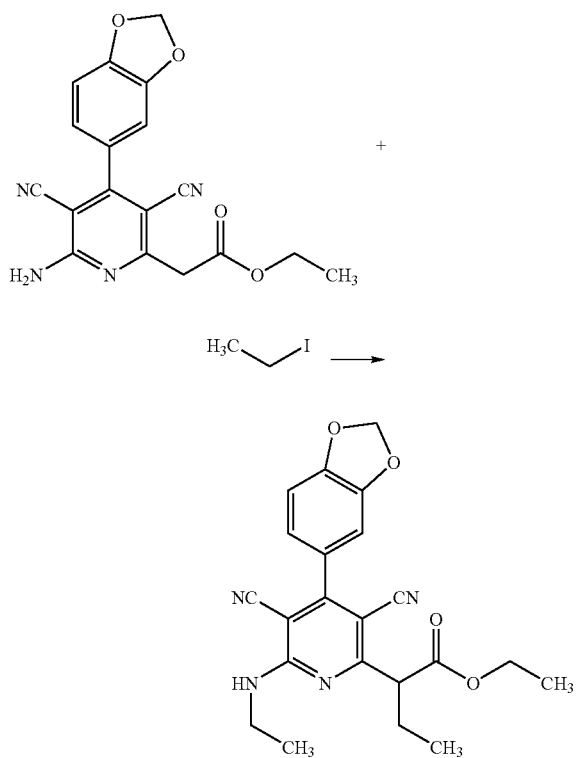

The compound is formed in the reaction of Example 4 and is isolated from the crude mixture by chromatographing the mixture using RP-HPLC and an acetonitrile/water gradient.

Yield: 13% of theory

ESI (positive) calc. 392.413. found [M+H] 393.2.

Example 6

Methyl 2-[6-amino-4-(1,3-benzodioxol-5-yl)-3,5-dicyano-2-pyridinyl]propionate

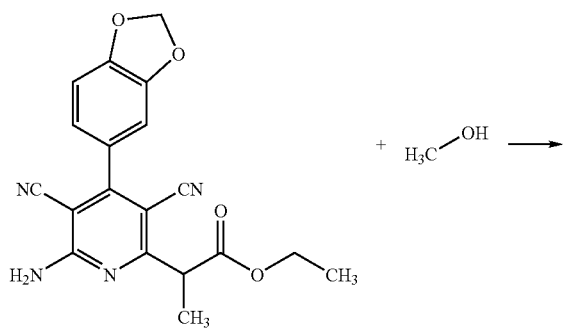

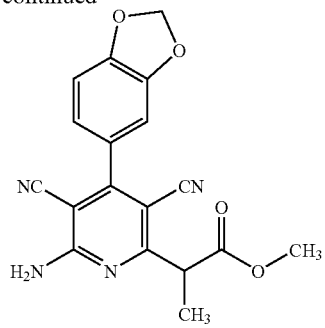

Ethyl 2-[6-amino-4-(1,3-benzodioxol-5-yl)-3,5-dicyano-2-pyridinyl]propionate (from Example 1) (50 mg, 0.137 mmol) is heated under reflux in methanol (2 ml) with a catalytic amount of sodium borohydride for 1.5 hours. 1 N hydrochloric acid and saturated sodium chloride solution are added. The aqueous phases are extracted twice with ethyl acetate and the combined organic phases are dried over magnesium sulfate, filtered and concentrated using a rotary evaporator. The product is isolated by RP-HPLC (Kromasil column 250 * 20 mm, C18, 10 μm; acetonitrile/water gradient: 3 minutes 10%, then within 30 minutes to 80%, flow rate: 25 ml*min$^{-1}$).

Yield: 24 mg (50% of theory).

$^1$H-NMR (200 MHz, DMSO-d$_6$): δ=1.45 (d, 3H), 3.64 (s, 3H), 4.16 (q, 1H), 6.16 (s, 2H), 7.07–7.20 (m, 3H), 7.98 (bs, 2H).

ESI (positive) calc. 350.33. found [M+H] 351.139.

The example compounds 7 to 9 described below are prepared analogously to Example 6, where methanol is replaced by the corresponding alcohol as solvent:

Example 7

Butyl 2-[6-amino-4-(1,3-benzodioxol-5-yl)-3,5-dicyano-2-pyridinyl]propionate

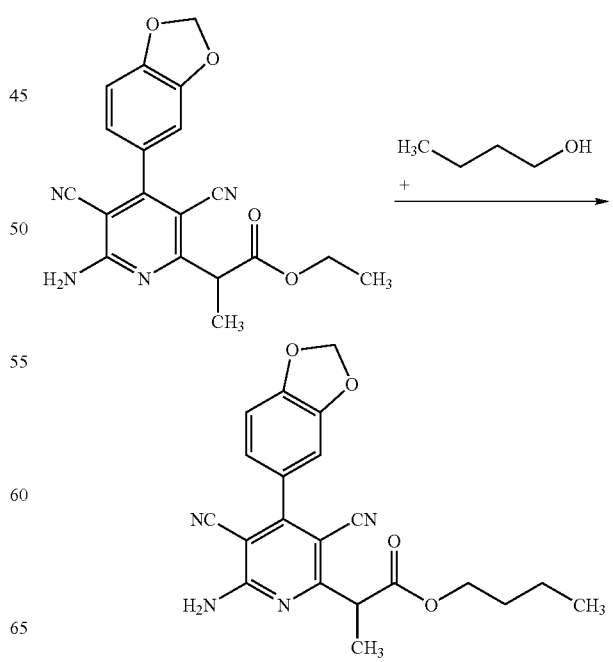

Yield: 47% of theory

¹H-NMR (200 MHz, DMSO-d₆): δ=1.42 (d, 3H), 1.52–1.77 (m, 2H), 1.88–2.05 (m, 2H), 2.20–2.30 (m, 2H), 4.11 (q, 1H), 4.87–4.97 (m, 1H), 6.16 (s, 2H), 7.03–7.19 (m, 3H), 7.97 (bs, 2H).

ESI (positive) calc. 390.4. found [M+H] 391.284.

Example 8

Isopropyl 2-[6-amino-4-(1,3-benzodioxol-5-yl)-3,5-dicyano-2-pyridinyl]propionate

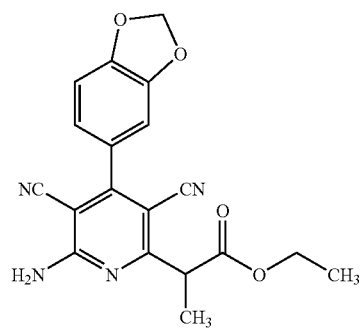

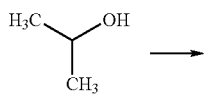

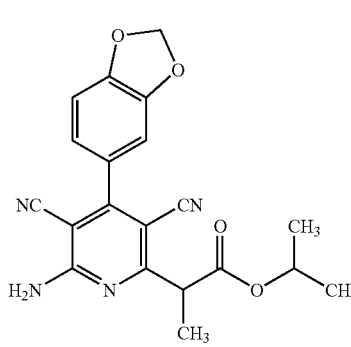

Yield: 21% of theory

¹H-NMR (200 MHz, DMSO-d₆): δ=1.16 (dd, 6H), 1.42 (d, 3H), 4.08 (q, 1H), 4.92–4.96 (m, 1H), 6.16 (s, 2H), 7.02–7.18 (m, 3H), 7.95 (bs, 2H).

ESI (positive) calc. 378.39. found [M+H] 379.26.

Example 9

Isobutyl 2-[4-(1,3-benzodioxol-5-yl)-3,5-dicyano-6-methylamino-2-pyridinyl]propionate

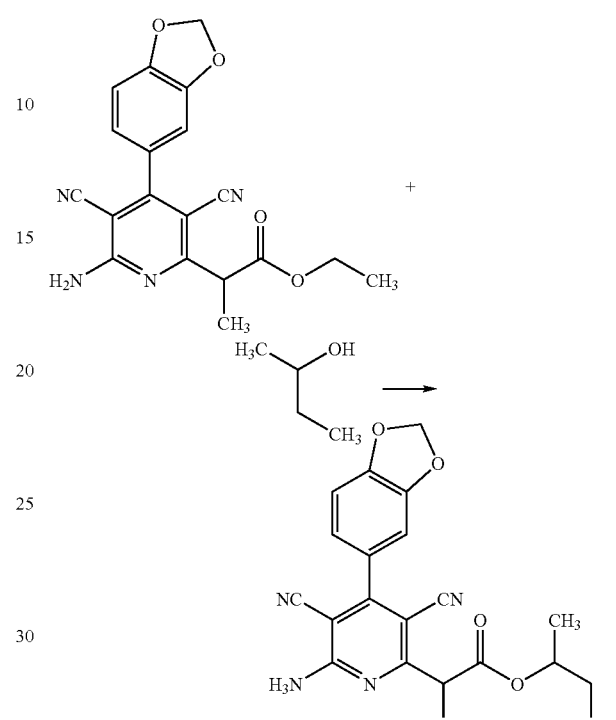

Yield: 20% of theory

ESI (positive) calc. 392.41. found 392.

Example 10

2-Amino-4-(1,3-benzodioxol-5-yl)-6-cyclopropyl-3,5-dicyanopyridine

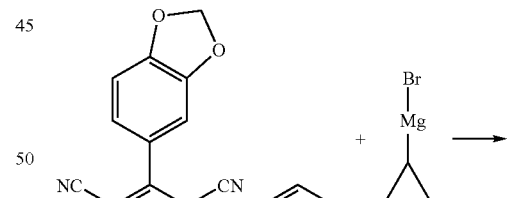

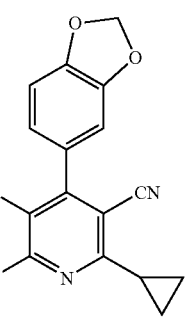

Under an atmosphere of argon, 2-amino-4-(1,3-benzodioxol-5-yl)-6-(phenyl-sulfanyl)-3,5-dicyanopyridine [preparation analogously to J. M. Quintela, J. L. Soto, Anales de Quimica 79, 368–372 (1983)] (100 mg, 0.27 mmol) is dissolved in absolute THF (3 ml). 1,3-Bis(diphenylphosphino)propanedichloronickel(II) (4.4 mg, 0.008 mmol) is added, the color of the solution changing to pink. On slow dropwise addition of cyclopropylmagnesium bromide (1M solution in THF; 0.644 ml, 0.644 mmol), a clear change in color to brown-red can be observed. The solution is heated at 50° C. for 3 hours. After only about 5 minutes, the solution turns green. 1N hydrochloric acid (1 ml) is added and the mixture is then diluted with diethyl ether. Solid sodium carbonate and water are added. The phases are separated and the organic phase is dried over magnesium sulfate, filtered and concentrated. The mixture is separated by silica gel column chromatography (toluene:ethyl acetate=2:1).

Yield: 15 mg (18% of theory)

$^1$H-NMR (200 MHz, DMSO-d$_6$): δ=1.07–1.17 (m, 4H), 2.18–2.50 (m, 1H), 6.15 (s, 2H), 7.01–7.16 (m, 3H), 7.71 (bs, 2H).

ESI (positive) calc. 304.31. found [M+H] 305.2.

The example compounds 11 and 12 described below are prepared analogously to Example 10:

Example 11

2-Amino-4-(1,3-benzodioxol-5-yl)-3,5-dicyano-6-(1-methyl-2-phenylethyl)-pyridine

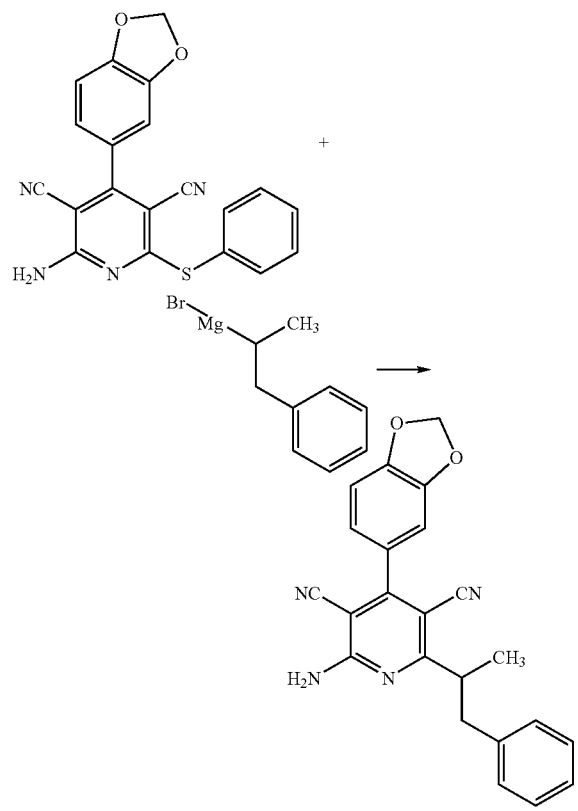

Yield: 43% of theory
ESI (positive) calc. 382.421. found [M+H] 383.

Example 12

2-Amino-4-(1,3-benzodioxol-5-yl)-6-(cyclopentyl)-3,5-dicyanopyridine

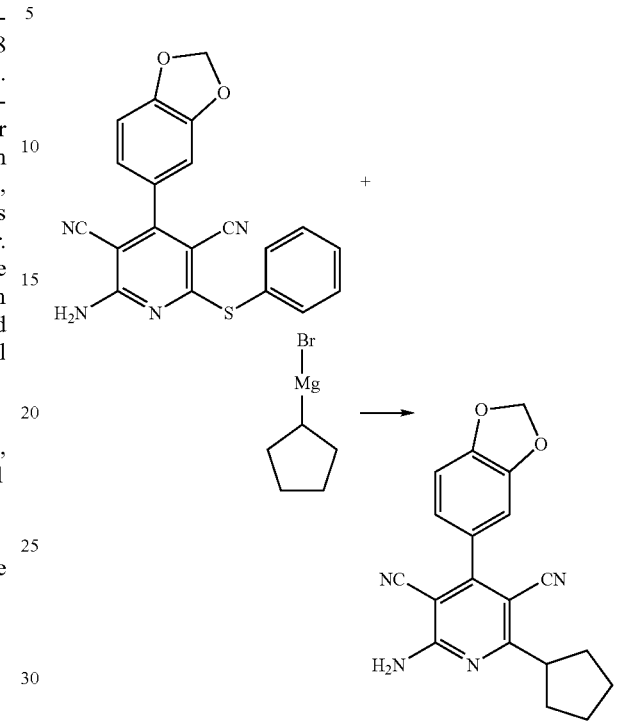

Yield: 27% of theory
ESI (positive) calc. 332.361. found [M+H] 333.1.

Example 13

Cyclobutyl 2-[6-amino-4-(1,3-benzodioxol-5-yl)-3,5-dicyano-2-pyridinyl]-propionate

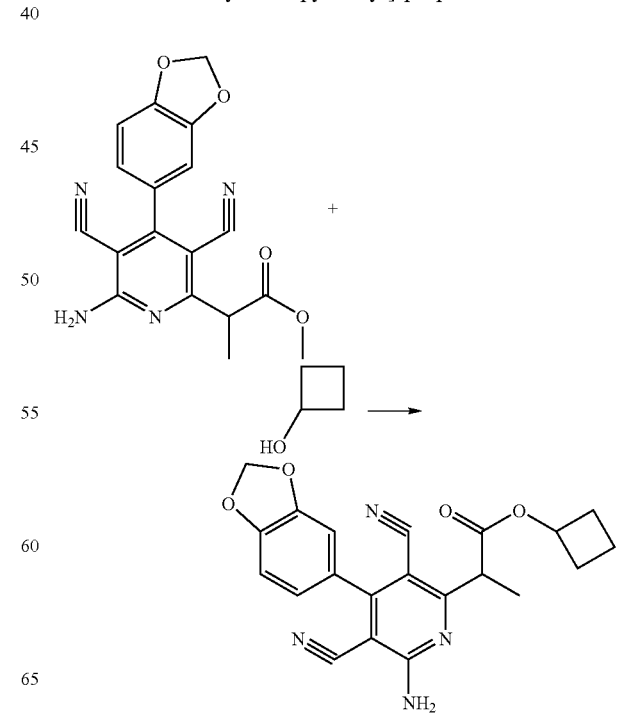

Methyl 2-[6-amino-4-(1,3-benzodioxol-5-yl)-3,5-dicyano-2-pyridinyl]propionate (from Example 6) (100 mg, 0.29 mmol) in cyclobutanol (5 ml) is heated under reflux with a catalytic amount of sodium hydride for 2.5 hours. The product is isolated by RP-HPLC (Kromasil column 250 * 20 mm, C18, 10 μm; acetonitrile/water gradient: 3 minutes 10%, then within 30 minutes to 80%, flow rate: 25 ml*min$^{-1}$).

Yield: 52 mg (46% of theory).

$^1$H-NMR (200 MHz, DMSO-d$_6$): δ=1.45 (d, 3H), 1.5–1.8 (m, 2H), 2.0 (m, 2H), 2.35 (m, 2H), 4.15 (q, 1H), 4.9 (q, 1H), 6.15 (s, 2H), 7.05–7.20 (m, 3H), 7.9 (bs, 2H).

ESI (positive) calc. 390. found [M+H] 391.

Example 14

2-Amino-4-(1,3-benzodioxol-5-yl)-6-(1-methyl-2-propenyl)-3,5-pyridine-dicarbonitrile

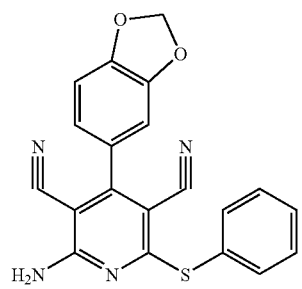

+

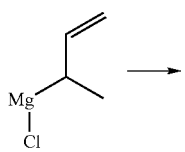

→

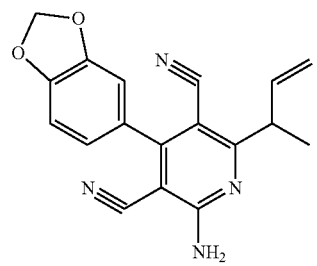

Preparation analogous to Example 10.

Yield: 74.6 mg (29% of theory)

$^1$H-NMR (200 MHz, DMSO-d6): δ=1.4 (d, 3H), 3.9 (q, 1H), 5.1 (m, 2H), 6.0 (m, 1H), 6.15 (s, 2H), 7.0–7.20 (m, 3H), 7.9 (bs, 2H).

ESI (positive) calc. 318. found [M+H] 319.

Example 15

2-Amino-4-(2,3-dihydro-1,4-benzodioxin-6-yl)-6-isopropyl-3,5-pyridine-dicarbonitrile

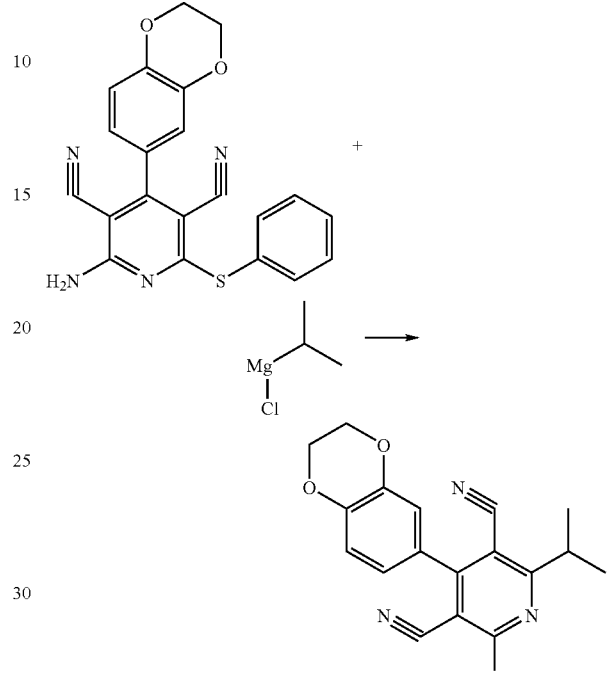

Preparation analogous to Example 10.

Yield: 64 mg (25% of theory).

$^1$H-NMR (200 MHz, DMSO-d$_6$): δ=1.25 (d, 6H), 4.0 (q, 1H), 4.35 (s, 4H), 7.0 (m, 3H), 7.8 (bs, 2H).

ESI (positive) calc. 320. found [M+H] 321.

Example 4

Step 1

Ethyl [6-amino-4-(2,3-dihydro-1,4-benzodioxin-6-yl)-3,5-dicyano-2-pyridinyl]-acetate

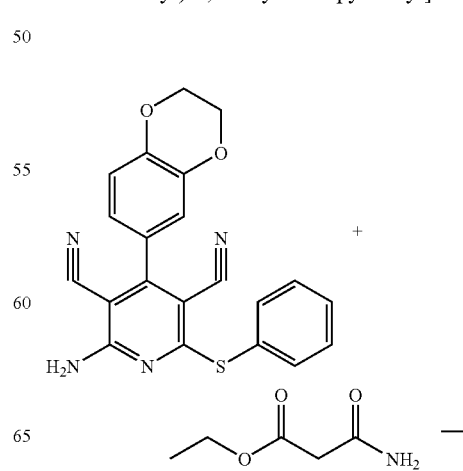

-continued

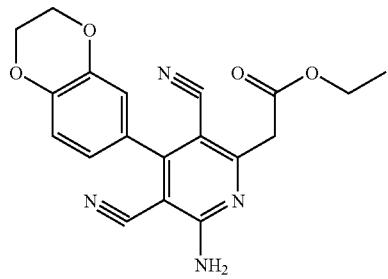

Preparation analogous to Example 1, step 1.

Yield: 462 mg (49% of theory)

ESI (positive) calc. 364. found [M+H] 365.

Step 2

Ethyl 2-[6-amino-4-(2,3-dihydro-1,4-benzodioxin-6-yl)-3,5-dicyano-2-pyridinyl]-propionate

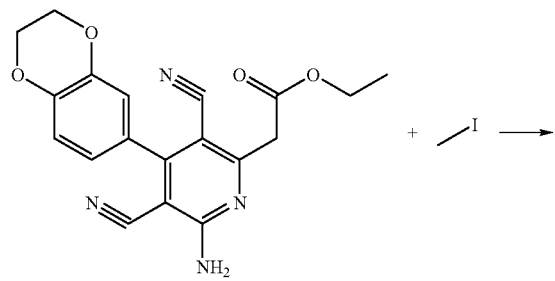

Preparation analogous to Example 1, step 2.

Yield: 258 mg (56% of theory).

$^1$H-NMR (200 MHz, DMSO-$d_6$): δ=1.15 (tr, 3H), 1.45 (d, 6H), 4.05 (q, 1H), 4.15 (q, 2H), 4.35 (s, 4H), 7.0 (m, 3H), 7.9 (bs, 2H).

ESI (positive) calc. 378. found [M+H] 379.

The invention claimed is:

1. A compound of the formula (I)

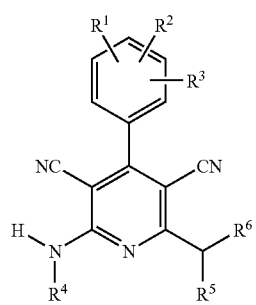

in which

R$^1$, R$^2$ and R$^3$ independently of one another represent (C$_1$–C$_8$)-alkyl which may be substituted up to three times by hydroxyl, (C$_1$–C$_4$)-alkoxy, (C$_3$–C$_7$)-cycloalkyl, (C$_2$–C$_4$)-alkenyl, (C$_2$–C$_4$)-alkynyl, halogen or (C$_6$–C$_{10}$)-aryloxy, (C$_6$–C$_{10}$)-aryl which may be substituted up to three times by halogen, nitro, (C$_1$–C$_4$)-alkoxy, carboxyl, (C$_1$–C$_4$)-alkoxycarbonyl or mono- or di-(C$_1$–C$_4$)-alkylamino, (C$_1$–C$_8$)-alkoxy which may be substituted by hydroxyl, (C$_1$–C$_4$)-alkoxy, (C$_3$–C$_7$)-cycloalkyl, (C$_2$–C$_4$)-alkenyl, (C$_6$–C$_{10}$)-aryl, 5- or 6-membered heteroaryl having up to three heteroatoms selected from the group consisting of N, O and S, (C$_6$–C$_{10}$-aryloxy, halogen, cyano, (C$_1$–C$_4$)-alkoxycarbonyl, (C$_1$–C$_4$)-alkanoyloxy, amino or mono- or di-(C$_1$–C$_4$)-alkylamino, hydrogen, hydroxyl, halogen, nitro, cyano or —NH—C(O)—R$^7$, in which R$^7$ represents (C$_1$–C$_8$)-alkyl which may be substituted by hydroxyl or (C$_1$–C$_4$)-alkoxy, (C$_3$–C$_7$)-cycloalkyl or (C$_6$–C$_{10}$)-aryl which may be substituted up to three times by, independently of one another, by halogen, nitro, (C$_1$–C$_4$)-alkoxy, carboxyl, (C$_1$–C$_4$)-alkoxycarbonyl or mono- or di-(C$_1$–C$_4$)-alkylamino, or R$^1$ and R$^2$ are attached to adjacent phenyl ring atoms and, together with the two ring carbon atoms, form a 5- to 7-membered saturated or partially unsaturated heterocycle having one or two heteroatoms selected from the group consisting of N, O and S which may be substituted by (C$_1$–C$_4$)-alkyl or oxo, R$^4$ represents hydrogen, (C$_1$–C$_8$)-alkyl which may be substituted by hydroxyl, (C$_1$–C$_4$)-alkoxy, (C$_3$–C$_7$)-cycloalkyl, (C$_6$–C$_{10}$)-aryl, 5- or 6-membered saturated or partially unsaturated heterocyclyl having up to three heteroatoms selected from the group consisting of N, O and S or 5- to 10-membered heteroaryl having up to three heteroatoms selected from the group consisting of N, O and S, or (C$_3$–C$_7$)-cycloalkyl which may be substituted by hydroxyl or (C$_1$–C$_8$)-alkyl, R$^5$ represents (C$_1$–C$_4$)-alkyl or (C$_1$–C$_4$)-alkoxy which may be mono- or disubstituted, independently of one another, by hydroxyl, (C$_1$–C$_4$)-alkoxy, (C$_3$–C$_7$)-cycloalkyl, (C$_6$–C$_{10}$)-aryl or 5- to 10-membered heteroaryl having up to three heteroatoms selected from the group consisting of N, O and S, where aryl and heteroaryl for their part may be substituted by halogen, (C$_1$–C$_4$)-alkyl, (C$_1$–C$_4$)-alkoxy, amino, mono- or di- ($C_1$–$C_4$)-alkylamino, nitro, cyano, trifluoromethyl or hydroxyl, or ($C_2$–$C_4$)-alkenyl, $R^6$ represents ($C_1$–$C_8$)-alkyl which may be substituted by hydroxyl, ($C_1$–$C_4$)-alkoxy, ($C_3$–$C_7$)-cycloalkyl, ($C_2$–$C_4$)-alkenyl, —CO—O—$R^8$, ($C_6$–$C_{10}$)-aryl or 5- to 10-membered heteroaryl having up to three heteroatoms selected from the group consisting of N, O and S where aryl and heteroaryl for their part may be substituted by halogen, ($C_1$–$C_4$)-alkyl, ($C_1$–$C_4$)-alkoxy, amino, mono- or di-($C_1$–$C_4$)-alkylamino, nitro, cyano, trifluoromethyl or hydroxyl, ($C_3$–$C_7$)-cycloalkyl or —CO—O—$R^8$, in which $R^8$ represents hydrogen, ($C_1$–$C_8$)-alkyl which may be substituted by hydroxyl or ($C_1$–$C_4$)-alkoxy, ($C_3$–$C_7$)-cycloalkyl or ($C_6$–$C_{10}$)-aryl which may be substituted up to three times, independently of one another, by halogen, nitro, ($C_1$–$C_4$)-alkoxy, carboxyl, ($C_1$–$C_4$)-alkoxycarbonyl or mono- or di-($C_1$–$C_4$)-alkylamino, or $R^5$ and $R^6$ together with the carbon atom to which they are attached form a 3- to 7-membered saturated or partially unsaturated ring which may contain one or two heteroatoms selected from the group consisting of N, O and S in the ring and which may be mono- to trisubstituted, independently of one another, by oxo, fluorine, chlorine, bromine, hydroxyl, ($C_1$–$C_6$)-alkyl or ($C_1$–$C_6$)-alkoxy, or a salt, a hydrate, a hydrate of a salt or a solvate thereof.

2. The compound as claimed in claim 1 in which $R^1$ and $R^2$ independently of one another represent hydrogen, ($C_1$–$C_6$)-alkyl, ($C_1$–$C_6$)-alkoxy which may be substituted by hydroxyl, ($C_1$–$C_4$)-alkoxy, ($C_1$–$C_4$)-alkanoyloxy or cyclopropyl, hydrogen, hydroxyl, fluorine, chlorine, nitro or —NH—C(O)—$CH_3$ or $R^1$ and $R^2$ are attached to adjacent phenyl ring atoms and represent a group —O—$CH_2$—O— or —O—$CH_2$—$CH_2$—O—, $R^3$ represents hydrogen, $R^4$ represents hydrogen, ($C_1$–$C_4$-alkyl which is substituted by hydroxyl, ($C_1$–$C_4$)-alkoxy or cyclopropyl, or represents cyclopropyl, $R^5$ represents ($C_1$–$C_4$)-alkyl which may be mono- or disubstituted, independently of one another, by ($C_3$–$C_6$)-cycloalkyl, phenyl, which for its part may be substituted by fluorine, trifluoromethyl or ($C_1$–$C_4$)-alkoxy, pyridyl, furyl or thienyl, or ($C_2$–$C_4$)-alkenyl, and $R^6$ represents ($C_1$–$C_4$)-alkyl or —CO—O—$R^8$ wherein $R^8$ is ($C_1$–$C_4$)-alkyl or $R^5$ and $R^6$ together with the carbon atom to which they are attached form a 3- to 7-membered saturated or partially unsaturated ring which may contain a heteroatom selected from the group consisting of N, O and S in the ring or a salt, a hydrate, a hydrate of a salt or a solvate thereof.

3. The compound as claimed in claim 1 or 2 in which $R^1$ represents hydrogen, chlorine, nitro, methyl, methoxy, ethoxy, n-propoxy, isopropoxy, n-butoxy, where the alkoxy radicals for their part may be substituted by hydroxyl, methoxy, ethoxy, n-propoxy, isopropoxy, n-butoxy, —O—C(O)—$CH_3$ or cyclopropyl, or —NH—C(O)—$CH_3$, $R^2$ represents hydrogen or $R^1$ and $R^2$ are attached to adjacent phenyl ring atoms and represent a group —O—$CH_2$—O—, $R^3$ represents hydrogen, $R^4$ represents hydrogen, methyl, ethyl, n-propyl, isopropyl, n-butyl, where the alkyl radicals for their part may be substituted by hydroxyl, methoxy, ethoxy, n-propoxy, isopropoxy, n-butoxy or cyclopropyl, or cyclopropyl, $R^5$ represents methyl, ethyl, n-propyl, isopropyl, n-butyl, where the alkyl radicals for their part may be mono- or disubstituted, independently of one another, by cyclopropyl, phenyl, which for its pan may be substituted by fluorine, trifluoromethyl or methoxy, pyridyl, furyl or thienyl, ethenyl, propenyl or butenyl and $R^6$ represents methyl, ethyl, n-propyl, isopropyl, n-butyl, methoxycarbonyl, ethoxycarbonyl, n-propoxycarbonyl, isopropoxycarbonyl, n-butoxycarbonyl or isobutoxycarbonyl or $R^5$ and $R^6$ together with the carbon atom to which they are attached form a cyclopropyl, cyclobutyl, cyclopentyl or cyclohexyl ring or a salt, a hydrate, a hydrate of a salt or a solvate thereof.

4. A process for preparing compounds of the formula (I) as defined in claim 1, wherein either (A) a compound of the formula (II)

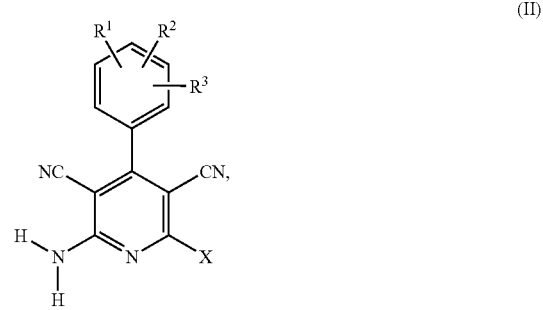

(II)

in which $R^1$, $R^2$ and $R^3$ are as defined in claim 1 and X represents a leaving group, is initially reacted with ethyl malonamide (III)

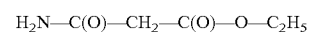

(III)

to give a compound of the formula (IV)

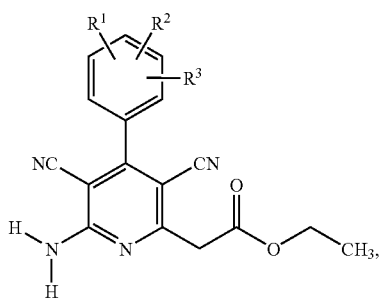
(IV)

in which
$R^1$, $R^2$ and $R^3$ are as defined in claim 1,
and then reacted with a compound of the formula (V)

$R^5—Y$ (V)

in which
$R^5$ is as defined in claim 1 and Y represents a leaving group
to give a compound of the formula (I)
in which
$R^1$, $R^2$, $R^3$, $R^4$ and $R^5$ are as defined in claim 1 and $R^6$ represents a radical —C(O)—O—$C_2H_5$,
and, if appropriate, subsequently reacted with a compound of the formula (VI)

$R^8$—OH (VI)

in which $R^8$ is as defined in claim 1
to give a compound of the formula (I)
in which
$R^6$ represents a radical —C(O)—O—$R^8$ and $R^1$, $R^2$, $R^3$, $R^4$, $R^5$ and $R^8$ are as defined in claim 1,
or
(B) a compound of the formula (II)
is reacted with a Grignard compound of the formula (VII)

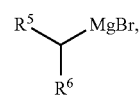
(VII)

in which
$R^5$ and $R^6$ are as defined in claim 1
to give a compound of the formula (I)
in which
$R^1$, $R^2$, $R^3$, $R^5$ and $R^6$ are as defined in claim 1 and $R^4$ represents hydrogen,
and, if appropriate, subsequently reacted wit a compound of the formula (VIII)

$R^4$—Y' (VIII)

in which
$R^4$ is as defined in claim 1 and Y' represents a leaving group.

5. A pharmaceutical composition, comprising at least one compound of the formula (I) as defined in claim 1 and a pharmaceutically acceptable carrier.

6. A method for the treatment of disorders of the cardiovascular system (cardiovascular disorders) comprising administering an effective amount of a compound of the formula (I) as defined in claim 1.

* * * * *